United States Patent
McKeown

(10) Patent No.: US 12,005,235 B2
(45) Date of Patent: Jun. 11, 2024

(54) DRUG DELIVERY SYSTEMS INCLUDING DISPLACEABLE CLOSURES

(71) Applicant: Eli Lilly and Company, Indianapolis, IN (US)

(72) Inventor: Gavin Miles McKeown, Bedford, MA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 32 days.

(21) Appl. No.: 17/772,304

(22) PCT Filed: Nov. 13, 2020

(86) PCT No.: PCT/US2020/060349
§ 371 (c)(1),
(2) Date: Apr. 27, 2022

(87) PCT Pub. No.: WO2021/101794
PCT Pub. Date: May 27, 2021

(65) Prior Publication Data
US 2022/0401651 A1 Dec. 22, 2022

Related U.S. Application Data

(60) Provisional application No. 62/937,444, filed on Nov. 19, 2019.

(51) Int. Cl.
*A61M 5/24* (2006.01)
*A61M 5/32* (2006.01)

(52) U.S. Cl.
CPC ........ *A61M 5/2455* (2013.01); *A61M 5/3293* (2013.01); *A61M 2005/2407* (2013.01)

(58) Field of Classification Search
CPC .......... A61M 5/2455; A61M 2005/247; A61M 5/24; A61M 2205/582; A61M 5/3293;
(Continued)

(56) References Cited

U.S. PATENT DOCUMENTS 6,132,395 A * 10/2000 Landau .................. A61M 5/30
604/249
2011/0143577 A1 6/2011 Su et al.
(Continued)

FOREIGN PATENT DOCUMENTS

WO 2011125562 11/2011

OTHER PUBLICATIONS

Patent Cooperation Treaty International Searching Report pertaining to International Application No. PCT/US2020/060349; International Filing Date: Nov. 13, 2020, dated Feb. 17, 2021.
(Continued)

*Primary Examiner* — Theodore J Stigell
*Assistant Examiner* — Nidah Hussain
(74) *Attorney, Agent, or Firm* — M. Daniel Spillman

(57) ABSTRACT

A drug delivery system includes a drug containing device and a drug delivery device. The drug containing device includes a chamber carrying a fluid drug and an outlet in fluid communication with the chamber. A first closure initially inhibits the fluid drug from exiting the drug containing device via the outlet. The drug delivery device includes a fluid passageway and a stem having an inlet in fluid communication with the fluid passageway. The stem displaces the first closure from the outlet and enters the outlet to provide fluid communication between the chamber and the fluid passageway and thereby facilitates delivery of the fluid drug to the drug delivery device. A second closure is coupled to the stem, and the second closure engages the first body at the outlet when the stem enters the outlet to inhibit the fluid drug from exiting the drug containing device around the stem.

20 Claims, 3 Drawing Sheets

(58) Field of Classification Search
CPC .......... A61M 2005/2407; A61M 5/285; A61M 2005/2474; A61J 1/20; A61J 1/2089
USPC ........................................................ 604/257
See application file for complete search history.

(56) References Cited

U.S. PATENT DOCUMENTS

| | | | | |
|---|---|---|---|---|
| 2015/0265500 A1* | 9/2015 | Russo | ................... | A61M 5/322 |
| | | | | 604/239 |
| 2017/0340807 A1* | 11/2017 | Bendix | ................. | A61M 5/326 |
| 2018/0169350 A1* | 6/2018 | Knapp | ................. | A61M 5/347 |
| 2018/0185584 A1* | 7/2018 | Cowe | ................. | A61M 5/2455 |

OTHER PUBLICATIONS

Patent Cooperation Treaty Written Opinion of the International Searching Authority pertaining to International Application No. PCT/US2020/060349; International Filing Date: Nov. 13, 2020, dated Feb. 17, 2021.

* cited by examiner

DRUG DELIVERY SYSTEMS INCLUDING DISPLACEABLE CLOSURES

FIELD OF THE DISCLOSURE

The present disclosure relates to drug delivery systems, and in particular, to drug delivery systems including a drug containing device and a drug delivery device that remain separate until a drug is ready to be administered to a patient.

BACKGROUND

Drug delivery systems for administering fluid drugs or medications to patients typically need to maintain clean and dry fluid paths until use. As a result, some drug delivery systems include a drug containing device, such as a vial, that remains separate from a drug delivery device, such as a device including a delivery needle for subcutaneous delivery of a drug, until the drug is administered to a patient. To provide an interface and facilitate drug delivery from the drug containing device to the drug delivery device, such systems may include an interface needle and pierceable septum. However, these components can be challenging to incorporate into small devices. For example, incorporating a needle into a drug delivery device can be difficult because it typically involves joining dissimilar materials and using different manufacturing processes. Specifically, incorporating a needle into a drug delivery device typically requires the use of adhesives, which may be problematic for high volume manufacture and detrimental to drug stability.

SUMMARY

According to an embodiment of the present disclosure, a system including a drug container having a tip end defined by a tip body. The tip body includes an outlet, and a pop-in seal is disposed at the outlet to contain a medication. The system includes a drug device having a device body and a device inlet in fluid communication with a fluid path extending within the device body away from the device inlet. The device body includes a stem extending within a recess defined in the device body. The stem defines the device inlet and includes a protruding stem body with a contact tip opposite a floor of the recess. The stem includes a sealing portion positioned along the protruding stem body, where a portion of the fluid path extends through the contact tip and the stem body. The drug container is removably coupled to the drug device. In a coupled configuration, the tip body of the drug container is slidably inserted into the recess of the drug device and a sealing edge of the outlet is in sealing engagement with the sealing portion of the stem subsequent to the contact tip engaging the pop-in seal to forcibly remove the pop-in seal from sealing engagement with the sealing edge.

According to another embodiment of the present disclosure, a drug delivery system includes a drug containing device and a drug delivery device. The drug containing device includes a first body including a chamber carrying a fluid drug, and an outlet in fluid communication with the chamber. The first body has an outer cross-sectional area. A first closure is detachably carried by the first body at the outlet and configured to inhibit the fluid drug from exiting the drug containing device via the outlet. The drug delivery device includes a second body including a recess defined therein and a fluid passageway defined therein. The recess has an inner cross-sectional area sized similar to the outer cross-sectional area to allow for a snug fit when the recess receives the first body. A stem extending within the recess from the second body and defining an inlet. The stem is configured to displace the first closure from the outlet and enter through the outlet. The inlet is configured to fluidly interconnect the chamber and the fluid passageway and thereby facilitate delivery of the fluid drug from the drug containing device to the drug delivery device. A second closure is associated with the stem, and the second closure is configured to engage the first body at the outlet when the stem enters the outlet to inhibit the fluid drug from exiting the drug containing device between the first body and the stem. A drug delivery element is in fluid communication with the fluid passageway.

According to yet another embodiment of the present disclosure, a drug delivery system has an uncoupled configuration and a coupled configuration. The drug delivery system includes a drug containing device including a first body including a chamber carrying a fluid drug and an outlet in fluid communication with the chamber. A first closure is detachably carried by the first body at the outlet. A drug delivery device includes a second body including a fluid passageway, and a stem coupled to the second body and including an inlet in fluid communication with the fluid passageway. A second closure is coupled to the stem. A drug delivery element is in fluid communication with the fluid passageway. In the uncoupled configuration, the first closure is carried by the first body at the outlet to inhibit the fluid drug from exiting the drug containing device via the outlet. In the coupled configuration, the first closure is displaced from the outlet by the stem, the second closure is engaged with the first body at the outlet, and the fluid drug is permitted to travel from the chamber to the fluid passageway via the inlet, for delivery to the drug delivery element.

BRIEF DESCRIPTION OF THE DRAWINGS

The above mentioned and other features of this present disclosure, and the manner of attaining them, will become more apparent and the invention itself will be better understood by reference to the following description of embodiments of the present disclosure taken in conjunction with the accompanying drawings, wherein.

Figure 1:
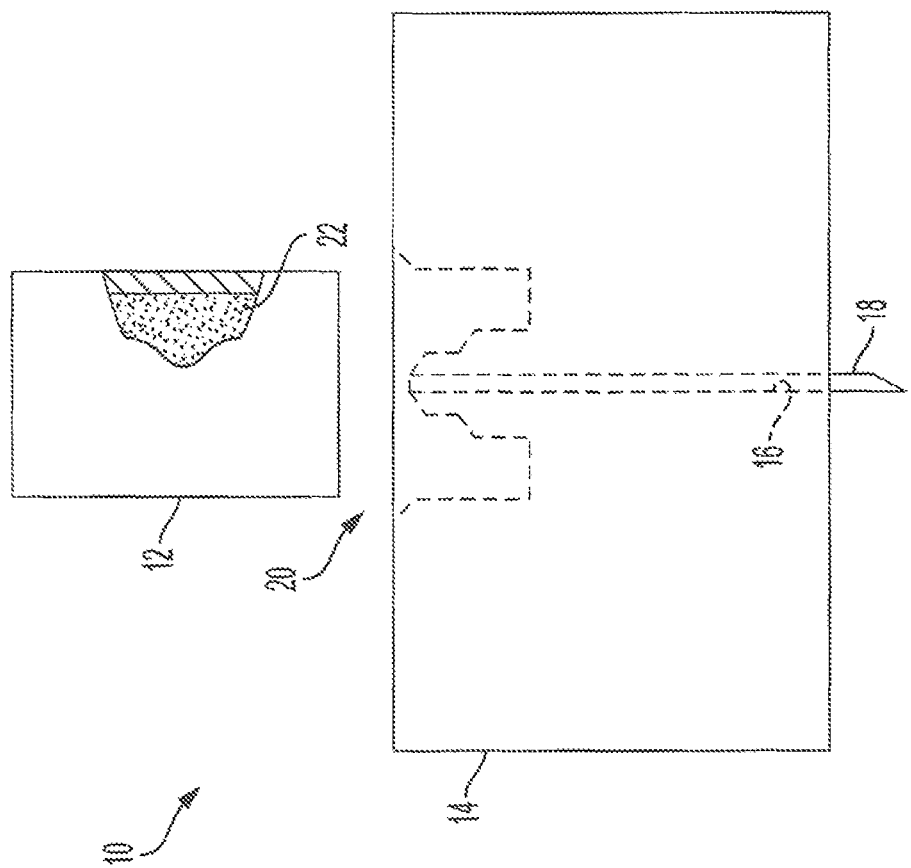
FIG. 1 is a side view of a drug-delivery system according to the present disclosure.

Corresponding reference characters indicate corresponding parts throughout the several views. Although the exemplification set out herein illustrates embodiments of the present disclosure, in several forms, the embodiments disclosed below are not intended to be exhaustive or to be construed as limiting the scope of the invention to the precise forms disclosed.

DETAILED DESCRIPTION

As described in further detail below, drug delivery systems according to some embodiments of the present disclosure include displaceable closures that advantageously provide simple and space-efficient structures for small coupling interfaces.

FIG. 1 illustrates a drug delivery system 10 according to an embodiment of the present disclosure. The drug delivery system 10 is illustratively shown as being an infusion device for subcutaneously delivering a fluid drug or medication 22, such as a diabetic treatment drug, for example insulin or the like, to a patient. However, drug delivery systems according to embodiments of the present disclosure may take various other forms, such as an injector device having a fillable reservoir, pump device having a fillable reservoir, or the like. Drug delivery systems according to embodiments of the present disclosure may deliver various other types of drugs, such as anesthetics, analgesics, steroids, epinephrine, or the like.

As illustrated in FIG. 1, the drug delivery system 10 generally includes a drug containing device 12, also referred to as a drug container or a vial, that carries a fluid drug 22. The drug containing device 12 removably couples to, and thereby selectively allows the movement of the fluid drug 22 from the device 12 to, a drug delivery device 14, also referred to as a drug device. The drug delivery device 14 includes a fluid passageway 16, also referred to as a fluid bore, for receiving the drug 22 and one or more drug delivery elements 18 (illustratively, a needle or cannula) for delivering the drug 22 to a patient. As described in further detail below, the drug containing device 12 and the drug delivery device 14 also define a coupling interface 20 that facilitates the movement of the drug 22 to the device 14 for the immediate or eventual delivery to a patient.

Figure 2:
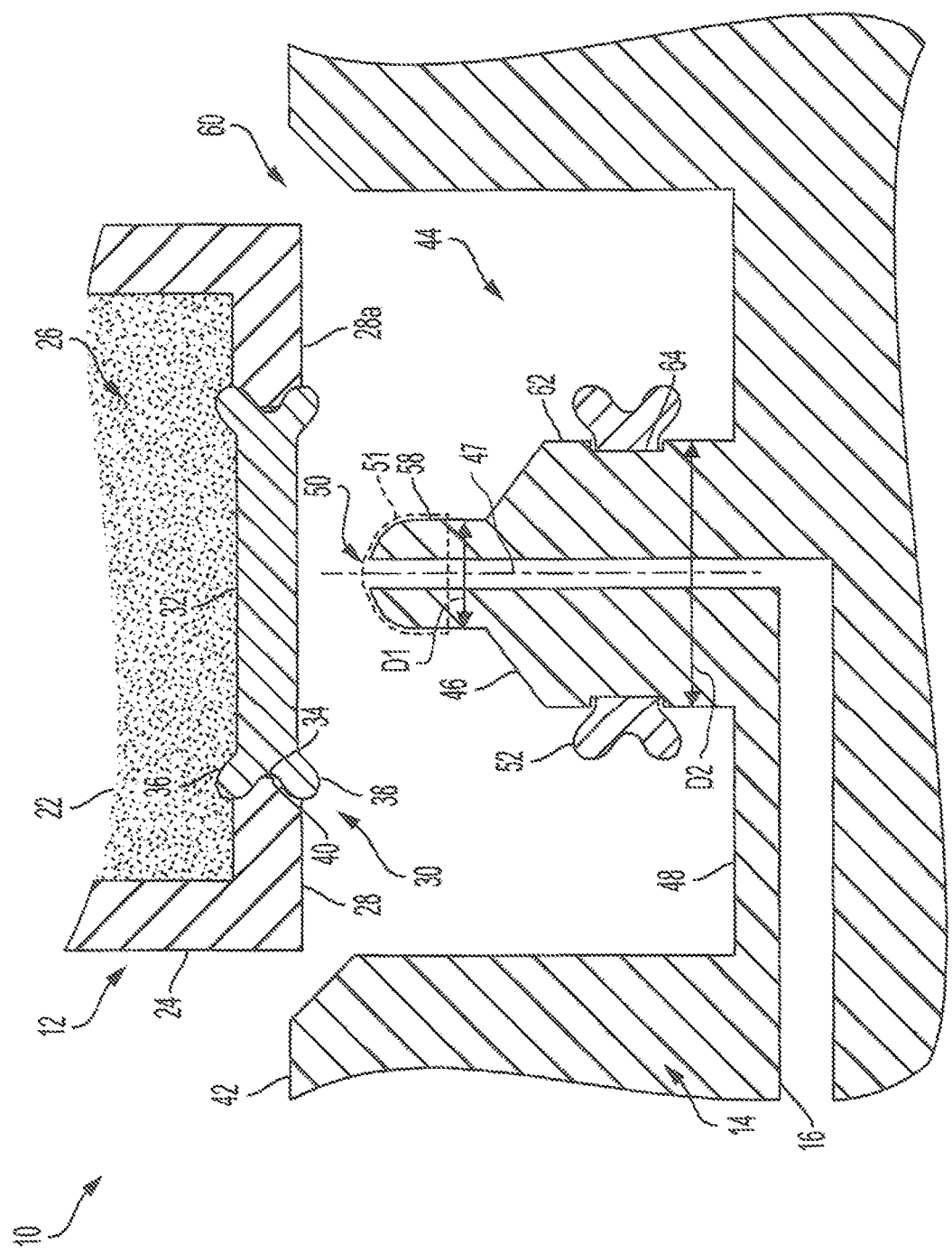
FIG. 2 is a partial sectional view of the drug delivery system of FIG. 1 illustrating a drug containing device and a drug delivery device in an uncoupled configuration.

FIG. 2 illustrates the drug delivery system 10 with the drug containing device 12 and the drug delivery device 14 in an uncoupled configuration, or an initial configuration, before the drug containing device 12 delivers the drug 22 to the drug delivery device 14. As illustrated, the drug containing device 12 includes a first, tip body 24 that defines a chamber 26 carrying the drug 22. Any portion of the first body of device 12 may be configured for insertion into the device 14. In one embodiment, the first body 24 also includes a tip end 28, that defines an outlet 30 in fluid communication with the chamber 26. The tip end 28 is shown along an axial end of the device 12, however, one in the art could associate the tip body along any side or end of the device 12. The axial end profile of the tip end 28 may be planar, as shown, or may have other shaped configurations such as being convexed or concaved. The first body 24 includes a first closure 32, also referred to as a pop-in seal, stopper, or plug, at the outlet 30. The first closure 32 is detachably coupled at the outlet 30. The outlet 30 defines a sealing edge 34 in initial sealing engagement with the outer circumference of the first closure 32, and the first closure 32 thereby initially inhibits the drug 22 from exiting the drug containing device 12 via the outlet 30 in this uncoupled configuration with the device 14.

With continued reference to FIG. 2, the first closure 32 is illustratively shown as having an outer profile similar to a quad o-ring or x-ring. That is, the first closure 32 includes a circumferentially extending upper lobe 36 and a circumferentially extending lower lobe 38 that each sealingly engage the drug containing device 12 at the outlet 30. Specifically, the upper lobe 36 sealingly engages the drug containing device 12 within the chamber 26 and the lower lobe 38 sealingly engages the drug containing device 12 outside of the chamber 26. In some embodiments, a circumferentially extending intermediate groove 40 is defined between the upper lobe 36 and the lower lobe 38 to facilitate maintaining the position of the first closure 32 between at the outlet 30, and the first closure 32 may receive relatively high forces before the upper lobe 36 and/or the lower lobe 38 deform and the first closure 32 moves away from the outlet 30. As illustrated, the upper lobe 36 and the lower lobe 38 may have substantially equal sizes (to facilitate, for example, ease of handling and assembly). Alternatively, the upper lobe 36 and the lower lobe 38 may have different sizes. As a specific example, the upper lobe 36 may be larger than the lower lobe 38 to facilitate resisting internal pressure in a headspace (not shown) within the chamber 26 of the drug containing device 12. In some embodiments, the first closure 32 advantageously provides a single piece closure that obviates a need of other devices to include a crimp cap to provide a compressive force needed to create a seal.

Figure 3:
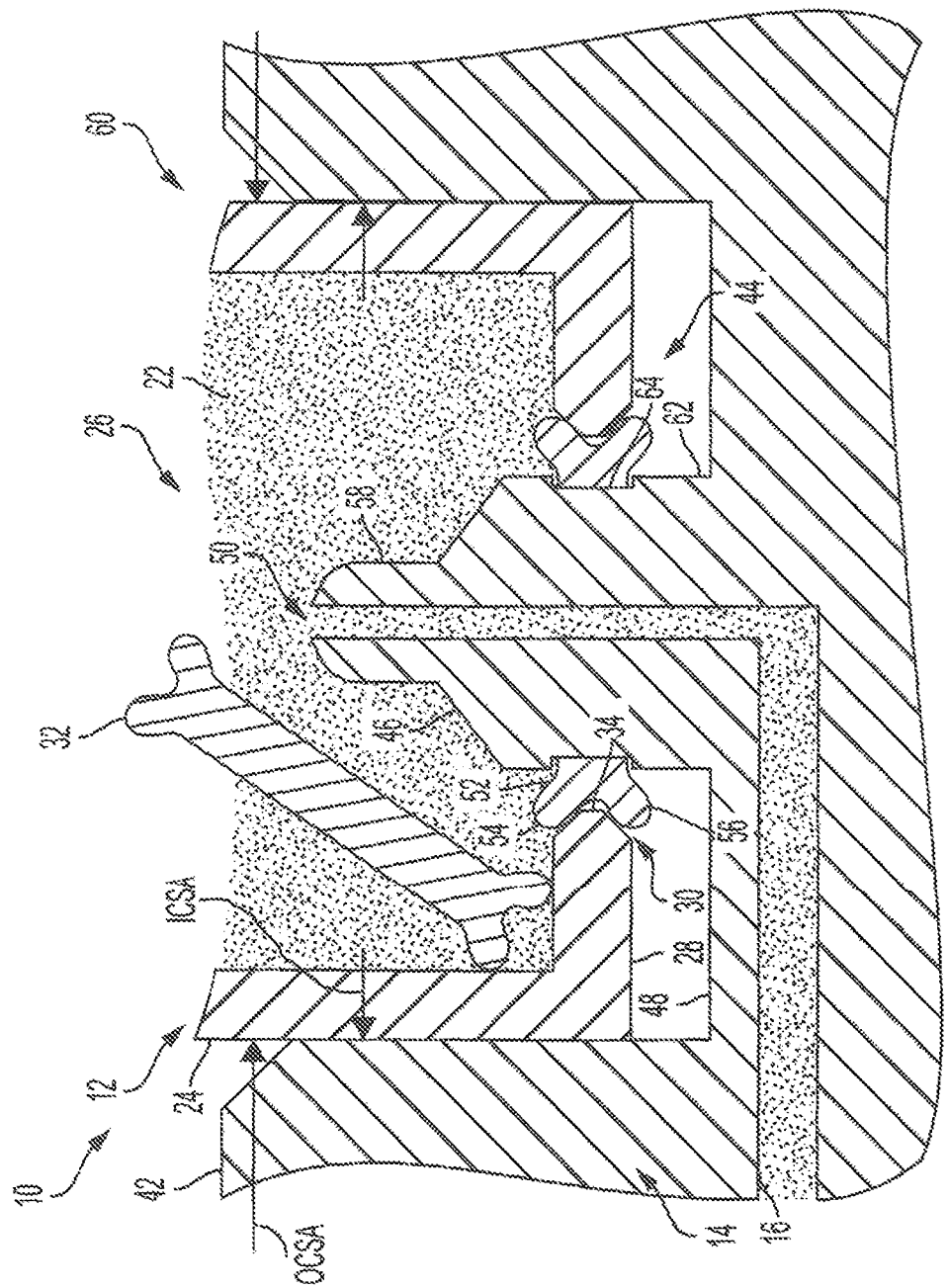
FIG. 3 is another partial sectional view of the drug delivery system of FIG. 1 illustrating the drug containing device and the drug delivery device in a coupled configuration.

FIG. 3 illustrates the drug delivery system 10 with the drug containing device 12 and the drug delivery device 14 in a coupled configuration. With reference to FIGS. 2-3, the drug delivery device 14 includes a second, device body 42 that defines an aspect of the coupling interface 20, which is complementarily configured together with the other aspect of the coupling interface 20 of the first body 24 of the drug containing device 12. More specifically, the second body 42 of the drug delivery device 14 includes a recess 44 defined therein that is sized and shaped to receive at least the end of the drug containing device 12 as shown in FIG. 3. In some embodiments and as illustrated, an inner cross-sectional area ICSA of the recess 44 is similar to an outer cross-sectional area OCSA of the drug containing device 12 at the tip end 28 to provide a snug fit, and in some embodiments a sealed fit. A stem 46 extends outwardly from a base surface 48, also referred to as a floor, of the recess 44 about a stem axis 47. The stem 47 can be referred to as an axial protruding body have an axial tip and a general radial outer surface defined about the axis 47. When the drug containing device 12 moves into the recess 44, the stem 46 displaces the first closure 32 from the outlet 30 and into the chamber 26, and the stem 46 enters in the chamber 26 through the open outlet 30. This action places an inlet 50 of the stem 46, which may be initially closed by a cap or plug 51 (shown in phantom lines in FIG. 2), in fluid communication with the chamber 26 of the drug containing device 12, and the inlet 50 thereby receives the drug 22 from the chamber 26. The inlet 50 of the stem 46 is in fluid communication with the fluid passageway 16 and delivers the drug 22 thereto. The fluid passageway 16 may deliver the drug 22 to the drug delivery element 18 (shown in FIG. 1) for delivery to the patient.

With continued reference to FIGS. 2 and 3, the stem 46 carries a second closure 52, also referred to as a seal, stopper, or plug, that replaces the first closure 32 when the stem 46 enters through the outlet 30. That is, the second closure 52 engages the first body 24 of the drug containing device 12 at the outlet 30 when the stem 46 enters the outlet 30 to inhibit the fluid drug 22 from exiting the drug containing device 12 between the first body 24 and the stem 46. Stated another way, the sealing edge 34 of the outlet 30 provides sealing engagement with the second closure 52 when the stem 46 enters the outlet 30. Near its outer perimeter, the second closure 52 may have a similar shape or a substantially identical shape to that of the first closure 32. The second closure 52 is illustratively shown as having an outer profile similar to a quad o-ring or x-ring. That is, the second closure 52 includes a circumferentially extending upper lobe 54 and a circumferentially extending lower lobe 56 that each sealingly engage the drug containing device 12 at the outlet 30 when the stem 46 enters the outlet 30. Specifically, the upper lobe 54 sealingly engages the drug containing device 12 within the chamber 26 and the lower lobe 56 sealingly engages the drug containing device 12 outside of the chamber 26. As illustrated, the upper lobe 54 and the lower lobe

56 may have substantially equal sizes. Alternatively, the upper lobe 54 and the lower lobe 56 many have different sizes.

With further reference to FIGS. 2 and 3, the stem 46 is illustratively shown as having an outer profile that varies in shape along a height direction. More specifically, the stem 46 includes a contact portion 58, also referred to as a contact tip, disposed proximate an opening 60 of the recess 44. The contact portion 58 is configured to engage and displace the first closure 32 from the outlet 30. As shown, the contact portion 58 defines the inlet 50 at an axial end of the stem 46; however, the inlet 50 may be disposed along a more radial outer surface of the stem body. In some embodiments, there can be more than one inlet feeding into one or more fluid passageways 16 (only one shown). The contact portion 58 has a first, relatively small, cross-sectional dimension in a width direction. For example, the contact portion 58 has a first, relatively small, diameter D1 when compared to a larger, lower portion of the stem body associated with a sealing portion 62 of the stem body. The contact portion 58 couples to the sealing portion 62, and the sealing portion 62 couples to the base surface 48 of the recess 44. The sealing portion 62 includes the second closure 52. The sealing portion 62 has a second, relatively large, cross-sectional diameter D2 in the width direction (compared to the contact portion 58). For example, the sealing portion 62 has a second, relatively large, diameter. The sealing portion 62 may include a circumferential recess 64 that receives the second closure 52 and prevents axial movement of the second closure 52 along the stem 46, particularly when the second closure 52 engages or disengages the drug containing device 12. Alternatively, the stem 46 may have different shapes and/or sizes. In some embodiments, the stem and the second closure are integrally or monolithically formed during a manufacturing process, such as in an injection molding.

In some embodiments and as illustrated, the stem 46 is integrally or monolithically formed with, or integrally or monolithically coupled to, the second body 42 of the drug delivery device 14. In such embodiments, the drug delivery device 14 may advantageously obviate a need of other delivery devices to join a body to a separate interface component, such as a needle comprising a potentially dissimilar material. In other embodiments, the stem 46 is not integrally or monolithically formed with, or integrally or monolithically coupled to, the second body 42 of the drug delivery device 14.

In some embodiments and as illustrated in FIG. 3, the drug containing device 12, in the coupled configuration, is spaced apart from the base surface 48 of the recess 44. Stated another way, when the sealing edge 34 is of the outlet 30 is engaged with the second closure 52, the axial end surface 28a of the tip end 28 of the drug containing device 12 is in a spaced relationship with the base surface 48 of the recess 44. In other embodiments, the axial end 28 of the drug containing device 12 contacts the base surface 48 of the recess 44 in the coupled configuration.

In some embodiments, in the coupled configuration the drug delivery system 10 may provide tactile and/or audible feedback. Stated another way, when the sealing edge 34 of the outlet 30 is engaged with the second closure 52, the system 10 may provide tactile and/or audible feedback.

In some embodiments, after delivery of the drug 22 from the drug containing device 12, the emptied drug containing device 12 may be detached from the drug delivery device 14. Stated another way, the sealing edge 34 of the outlet 30 may be disengaged from the second closure 52 such that the emptied drug containing device 12 is removed from the recess 44 of the drug delivery device 14. The drug delivery device 14 would then be exposed and free to receive a new drug containing device 12 subsequently.

While embodiments of the invention have been described as having exemplary designs, the embodiments of the present disclosure may be further modified within the spirit and scope of this disclosure. This application is therefore intended to cover any variations, uses, or adaptations of the disclosed embodiments using its general principles.

Various aspects are described in this disclosure, which include, but are not limited to, the following aspects:

A system including a drug container and a drug device, as described herein.

1. A system including: a drug container having a tip end defined by a tip body, the tip body having an outlet, and a pop-in seal disposed at the outlet to contain a medication, a drug device having a device body and a device inlet in fluid communication with a fluid path extending within the device body away from the device inlet, the device body including a stem extending within a recess defined in the device body, the stem defining the device inlet and including a protruding stem body with a contact tip opposite a floor of the recess, the stem including a sealing portion positioned along the protruding stem body, wherein a portion of the fluid path extends through the contact tip and the stem body, wherein the drug container is removably coupled to the drug device, wherein in a coupled configuration, the tip body of the drug container is slidably inserted into the recess of the drug device and a sealing edge of the outlet is in sealing engagement with the sealing portion of the stem subsequent to the contact tip engaging the pop-in seal to forcibly remove the pop-in seal from sealing engagement with the sealing edge.

2. The system of aspect 1, wherein, when the sealing edge is engaged with the sealing portion of the stem, an axial end surface of the tip end is in a spaced relationship with the floor of the recess.

3. The system of any one of aspects 1-2, wherein an outer cross-sectional area of the tip body is similar to an inner cross-sectional area of the recess to allow for a snug fit.

4. The system of any one of aspects 1-3, wherein each of the sealing portion of the stem and an edge of the pop-in seal has a lobed configuration configured to provide tactile and/or audible feedback.

5. The system of any one of aspects 1-4, wherein, after delivery of the medication from the drug container, the drug container is decoupled from to the drug device where the sealing edge is disengaged from the sealing portion of the stem such that the outlet of the drug container is removed from the recess of the drug device.

6. The system of any one of aspects 1-5, further including a cap or plug to close off an entrance of the fluid path at the contact tip.

7. A drug delivery system including: a drug containing device including: a first body comprising a chamber carrying a fluid drug, and an outlet in fluid communication with the chamber, the first body having an outer cross-sectional area; and a first closure detachably carried by the first body at the outlet and configured to inhibit the fluid drug from exiting the drug containing device via the outlet; and a drug delivery device including: a second body including a recess defined therein and a fluid passageway defined therein, the recess having an inner cross-sectional area sized similar to the outer cross-sectional area to allow for a snug fit when the recess receives the first body; a stem extending within the recess from the second body and defining an inlet, the stem configured to displace the first closure from the outlet and enter through the outlet, wherein the inlet is configured to fluidly interconnect the chamber and the fluid passageway and thereby facilitate delivery of the fluid drug from the drug containing device to the drug delivery device; a second closure associated with the stem, the second closure configured to engage the first body at the outlet when the stem enters the outlet to inhibit the fluid drug from exiting the drug containing device between the first body and the stem; and a drug delivery element in fluid communication with the fluid passageway.

8. The system of aspect 7, wherein the stem further includes: a contact portion configured to engage and displace the first closure from the outlet, the contact portion having a first cross-sectional dimension; and a sealing portion carrying the second closure, the sealing portion having a second cross-sectional dimension, the second cross-sectional dimension being greater than first cross-sectional dimension.

9. The system of aspect 8, wherein the first cross-sectional dimension is a first diameter and the second cross-sectional dimension is a second diameter.

10. The system of aspect 8 or 9, wherein the contact portion includes the inlet.

11. The system of any one of aspects 7-10, wherein the first closure includes an upper lobe configured to initially sealingly engage the drug containing device within the chamber.

12. The system of any one of aspects 7-11, wherein the first closure includes a lower lobe configured to initially sealingly engage the drug containing device outside of the chamber.

13. The system of any one of aspects 7-12, wherein the second closure includes an upper lobe configured to sealingly engage the drug containing device within the chamber when the stem enters the outlet.

14. The system of any one of aspects 7-13, wherein the second closure includes a lower lobe configured to sealingly engage the drug containing device outside of the chamber when the stem enters the outlet.

15. The system of any one of aspects 7-14, wherein the stem is monolithically formed with the second body.

16. A drug delivery system having an uncoupled configuration and a coupled configuration, the drug delivery system including: a drug containing device including: a first body including a chamber carrying a fluid drug and an outlet in fluid communication with the chamber; and a first closure detachably carried by the first body at the outlet; and a drug delivery device including: a second body including a fluid passageway; a stem coupled to the second body and including an inlet in fluid communication with the fluid passageway; a second closure coupled to the stem; and a drug delivery element in fluid communication with the fluid passageway; wherein: in the uncoupled configuration, the first closure is carried by the first body at the outlet to inhibit the fluid drug from exiting the drug containing device via the outlet; and in the coupled configuration, the first closure is displaced from the outlet by the stem, the second closure is engaged with the first body at the outlet, and the fluid drug is permitted to travel from the chamber to the fluid passageway via the inlet, for delivery to the drug delivery element.

17. The system of aspect 16, wherein the first closure includes an upper lobe that sealingly engages the drug containing device within the chamber in the uncoupled configuration.

18. The system of aspect 16 or 17, wherein the first closure includes a lower lobe that sealingly engages the drug containing device outside of the chamber in the uncoupled configuration.

19. The system of any one of aspects 16-18, wherein the second closure includes an upper lobe that sealingly engages the drug containing device within the chamber in the coupled configuration.

20. The system of any one of aspects 16-19, wherein the second closure includes a lower lobe that sealingly engages the drug containing device outside of the chamber in the coupled configuration.

What is claimed is:

1. A system including:
a drug container having a tip end defined by a tip body, the tip body having an outlet, and a pop-in seal disposed at the outlet to contain a medication, and
a drug device having a device body and a device inlet in fluid communication with a fluid path extending within the device body away from the device inlet, the device body including a stem extending within a recess defined in the device body, the stem defining the device inlet and including a protruding stem body with a contact tip opposite a floor of the recess, the stem including a sealing portion comprising a circumferentially extending lobe positioned along the protruding stem body, wherein a portion of the fluid path extends through the contact tip and the stem body,
wherein the drug container is removably coupled to the drug device, wherein in a coupled configuration, the tip body of the drug container is slidably inserted into the recess of the drug device and a sealing edge of the outlet is in sealing engagement with the circumferentially extending lobe of the sealing portion of the stem subsequent to the contact tip engaging the pop-in seal to forcibly remove the pop-in seal from sealing engagement with the sealing edge.

2. The system of claim 1, wherein, when the sealing edge is engaged with the sealing portion of the stem, an axial end surface of the tip end is in a spaced relationship with the floor of the recess.

3. The system of claim 1, wherein an outer cross-sectional area of the tip body is similar to an inner cross-sectional area of the recess to allow for a snug fit.

4. The system of claim 1, wherein an edge of the pop-in seal has a lobed configuration configured to provide tactile and/or audible feedback.

5. The system of claim 1, wherein the drug container is configured to be decoupled from the drug device, after delivery of the medication from the drug container, where the sealing edge is disengaged from the sealing portion of the stem such that the outlet of the drug container is removed from the recess of the drug device.

6. The system of claim 1, further comprising a cap or plug to close off an entrance of the fluid path at the contact tip.

7. A drug delivery system comprising:
a drug containing device comprising:
a first body comprising a chamber carrying a fluid drug, and an outlet in fluid communication with the chamber, the first body having an outer cross-sectional area; and
a first closure detachably carried by the first body at the outlet and configured to inhibit the fluid drug from exiting the drug containing device via the outlet; and
a drug delivery device comprising:
a second body including a recess defined therein and a fluid passageway defined therein, the recess having an inner cross-sectional area sized similar to the outer cross-sectional area to allow for a snug fit when the recess receives the first body;

a stem extending within the recess from the second body and defining an inlet, the stem configured to displace the first closure from the outlet and enter through the outlet, wherein the inlet is configured to fluidly interconnect the chamber and the fluid passageway and thereby facilitate delivery of the fluid drug from the drug containing device to the drug delivery device;

a second closure associated with the stem, the second closure configured to engage the first body at the outlet when the stem enters the outlet to inhibit the fluid drug from exiting the drug containing device between the first body and the stem; and a drug delivery element in fluid communication with the fluid passageway.

8. The system of claim 7, wherein the stem further comprises:
a contact portion configured to engage and displace the first closure from the outlet, the contact portion having a first cross-sectional dimension; and
a sealing portion carrying the second closure, the sealing portion having a second cross-sectional dimension, the second cross-sectional dimension being greater than the first cross-sectional dimension.

9. The system of claim 8, wherein the first cross-sectional dimension is a first diameter and the second cross-sectional dimension is a second diameter.

10. The system of claim 8, wherein the contact portion comprises the inlet.

11. The system of claim 7, wherein the first closure comprises an upper lobe configured to initially sealingly engage the drug containing device within the chamber.

12. The system of claim 7, wherein the first closure comprises a lower lobe configured to initially sealingly engage the drug containing device outside of the chamber.

13. The system of claim 7, wherein the second closure comprises an upper lobe configured to sealingly engage the drug containing device within the chamber when the stem enters the outlet.

14. The system of claim 7, wherein the second closure comprises a lower lobe configured to sealingly engage the drug containing device outside of the chamber when the stem enters the outlet.

15. The system of claim 7, wherein the stem is monolithically formed with the second body.

16. A drug delivery system having an uncoupled configuration and a coupled configuration, the drug delivery system comprising:
a drug containing device comprising:
a first body comprising a chamber carrying a fluid drug and an outlet in fluid communication with the chamber; and
a first closure detachably carried by the first body at the outlet; and
a drug delivery device comprising:
a second body comprising a fluid passageway;
a stem coupled to the second body and comprising an inlet in fluid communication with the fluid passageway;
a second closure coupled to the stem; and
a drug delivery element in fluid communication with the fluid passageway;
wherein:
in the uncoupled configuration, the first closure is carried by the first body at the outlet to inhibit the fluid drug from exiting the drug containing device via the outlet; and
in the coupled configuration, the first closure is displaced from the outlet by the stem, the second closure is engaged with the first body at the outlet, and the fluid drug is permitted to travel from the chamber to the fluid passageway via the inlet, for delivery to the drug delivery element.

17. The system of claim 16, wherein the first closure comprises an upper lobe that sealingly engages the drug containing device within the chamber in the uncoupled configuration.

18. The system of claim 16, wherein the first closure comprises a lower lobe that sealingly engages the drug containing device outside of the chamber in the uncoupled configuration.

19. The system of claim 16, wherein the second closure comprises an upper lobe that sealingly engages the drug containing device within the chamber in the coupled configuration.

20. The system of claim 16, wherein the second closure comprises a lower lobe that sealingly engages the drug containing device outside of the chamber in the coupled configuration.

* * * * *